(12) United States Patent
Ganju

(10) Patent No.: US 10,517,855 B1
(45) Date of Patent: Dec. 31, 2019

(54) INTERLEUKINS ACTIVITY INHIBITING COMPOSITION

(71) Applicant: Shibban Krishen Ganju, Oak Brook, IL (US)

(72) Inventor: Shibban Krishen Ganju, Oak Brook, IL (US)

( * ) Notice: Subject to any disclaimer, the term of this patent is extended or adjusted under 35 U.S.C. 154(b) by 0 days.

(21) Appl. No.: 16/271,644

(22) Filed: Feb. 8, 2019

(51) Int. Cl.
| | | |
|---|---|---|
| *A61K 31/437* | (2006.01) | |
| *A61K 9/00* | (2006.01) | |
| *A61K 9/48* | (2006.01) | |
| *A61K 47/10* | (2017.01) | |
| *A61K 47/12* | (2006.01) | |
| *A61K 47/44* | (2017.01) | |
| *A61K 47/46* | (2006.01) | |
| *A61K 47/34* | (2017.01) | |
| *A61K 47/14* | (2017.01) | |

(52) U.S. Cl.
CPC .......... *A61K 31/437* (2013.01); *A61K 9/0014* (2013.01); *A61K 9/4866* (2013.01); *A61K 47/10* (2013.01); *A61K 47/12* (2013.01); *A61K 47/14* (2013.01); *A61K 47/34* (2013.01); *A61K 47/44* (2013.01); *A61K 47/46* (2013.01)

(58) Field of Classification Search
None
See application file for complete search history.

(56) References Cited

U.S. PATENT DOCUMENTS

| | | |
|---|---|---|
| 5,290,553 A | 3/1994 | Iwu et al. |
| 2007/0048396 A1 | 3/2007 | Holland et al. |

FOREIGN PATENT DOCUMENTS

| | | |
|---|---|---|
| WO | WO 2007066928 A1 | 6/2007 |

*Primary Examiner* — Jared Barsky
(74) *Attorney, Agent, or Firm* — Intellectual Property Law Group LLP

(57) ABSTRACT

The present invention relates to interleukins (IL 17 and IL12/23) activity inhibiting composition. Further the present invention is related to novel compositions comprising active pharmaceutical ingredient, optionally in combination with other active pharmaceutical ingredients which are capable of treating the skin diseases or disorders and inhibiting the interleukins (IL 17 and IL12/23) activity. The present invention composition Alstonine compound, an emulsifier, an opacifier, a lubricant, a non-ionic surfactant and excipients including demineralized water.

4 Claims, No Drawings

INTERLEUKINS ACTIVITY INHIBITING COMPOSITION

FIELD OF THE INVENTION

The present invention relates to a interleukins 12/23 and 17 activity inhibiting composition. The present invention further relates to a pharmaceutical composition for mitigating or minimizing the skin related disorders and or diseases. The further invention is related to compositions useful for topical and oral use. The present invention further relates to compositions comprising alstonine, as the most active ingredient. The present invention further optionally comprises other active ingredients capable of mitigating or minimizing the skin related disorders and or diseases.

BACKGROUND OF THE INVENTION

Cytokines are a broad and loose category of small proteins (~5-20 kDa) that are important in cell signaling. Their release has an effect on the behavior of cells around them. Cytokines are involved in autocrine signaling, paracrine signaling and endocrine signaling as immunomodulating agents. Cytokines include chemokines, interferons, interleukins, lymphokines, and tumor necrosis factors (TNF). Cytokines play an important role in cellular communication. They regulate immunity, inflammation, cell activation, cell migration, cell proliferation, apoptosis, and hematopoiesis. Cytokine inhibitions are also used in treatment of various diseases such as autoimmune diseases (multiple sclerosis and vasculitis), tumor immunotherapy, skin related diseases and rheumatoid arthritis. But cytokine treatment has their fair share of side effects, when released persistently they can result in chronic disease. During the studies of the inflammatory diseases it is found that the certain inflammatory skin diseases have been associated with overproduction of cytokines, alteration in cytokine receptors, or dysregulation of cytokines. The study on the cytokines treatments has proven that the sometimes the cytokines treatment results in deleterious consequences such as flu-like reactions, vascular leak syndrome, fatigue, diarrhea, skin related diseases, thrombocytopenia, shock, respiratory distress, coma, and fatal hypotension.

In order to treat the cytokines related diseases, anti-cytokine therapy is used. The anti-cytokine therapy specifically targets cytokines e.g. TNF and Interleukins (because they are specifically responsible for the inflammation). It is shown in the studies that the inhibition of one cytokine can stop the process of immune system self-activation. The anti-cytokine therapy is used in treatment of skin related diseases such as Psoriasis Eczema, acne lichen planus, atopic dermatitis, and phemphigus. The anti-cytokine therapy has brought a big change in the field of the medicine. But anti cytokine treatment also effects the fundamental protective functions of the body. The anti-cytokine therapy may result in latent microbial infection, demyelinating, secondary autoimmune manifestation, symptoms of lupus erythematosus and inhibition of the cytokine also results in an abundant secretion of interferon α which can lead to thromboembolism. Also, the anti-cytokine therapy is expensive and not every patient can afford this treatment. Another disadvantage with the anti-cytokine therapy is that the it uses oral route for drug administration which is unsuitable for patients which are uncooperative or cannot use their mouth. The drugs administered through oral routes absorbs very slowly in-patient body.

So, there is a need of such novel topical composition which can modulate the cytokines without causing any harm. Alstonine is an alkaloid found in *Vinca minor* and *Aspidosperma* which have significance in treating skin related disorder. In the existing arts, alstonine is not defined properly for treatment of skin related problems and modulating the activity of interleukins (IL 17 and IL 12/23).

U.S. Pat. No. 5,290,553A discloses the extraction of alkaloids and their use in treating protozoan induced diseases especially for the treatment of malaria. According to the said disclosure wherein the plant *Picralima nitida* contains several indole and dihydroindole alkaloids, of which the major ones include akuammiline, akuammidine, akuammine, akuammigine, akuammicine, picraline and picraphylline. The principal alkaloid found in the plant, akuammine, has been shown to be inactive against avian malaria and in clinical trials. This citation does not refer to akuammicine-N-Oxide composition for the treatment of skin related disorders or diseases. Further this citation does not through light on any composition to treat skin relate disorders or diseases. Further this citation does not refer any such composition useful to prepare topical cream to treat skin related disorders or diseases.

WO2007066928A1 discloses an extract of *Caesalpinia sappan* L. having an angiogenesis inhibition activity and a use of the compound isolated therefrom, more precisely an extract of *Caesalpinia sappan* L. extracted by using water, alcohol or a mixture thereof, and a use of brazilin, sappanchalcone and brazilein isolated from the extract as an angiogenesis inhibitor. The extract of *Caesalpinia sappan* L. of the invention and a compound isolated therefrom have angiogenesis inhibition activity, so that they can be effectively used for the prevention and treatment of angiogenesis associated diseases such as vascular diseases, cardiovascular diseases, ophthalmic diseases, chronic inflammatory diseases, dermatological diseases, Alzheimer's disease, obesity and cancer.

US20070048396A1 discloses anti-inflammatory compositions comprising (a) an anti-inflammatory agent selected from the group consisting of olive leaf extract, holly herb, *sappan* wood, feverfew, and combinations of two or more thereof, and (b) an anti-inflammatory agent comprising at least one lipophilic aminoacid and at least one metal salt. Also provided are personal care products comprising such compositions, and methods of use thereof.

There is no indication from the existing art that alstonine compositions are useful in the treatment of skin related disorders or diseases. Therefore, the present invention discloses novel compositions useful in treating the skin related disorders or diseases.

SUMMARY OF THE INVENTION

The present invention is related to novel compositions comprising active pharmaceutical ingredient, optionally in combination with other active pharmaceutical ingredients which are capable of treating the skin diseases or disorders and inhibiting the IL 17 and IL12/23. The present invention composition includes DM Water, Glycerine, alstonine, Cetyl palmitate, Glyceryl Monostearate, Shea butter, Cetyl alcohol, Polysorbate 80, Cetostearyl Alcohol, Coconut oil, Dimethicone, BHA, BHT, Phenoxyethanol and Ethylhexylglycerin (Euxyl PE 9010). The present invention further relates to different pharmaceutical compositions that have different mode of application. Particularly, the present invention relates to pharmaceutical compositions that comprises alstonine.

OBJECTIVES OF THE PRESENT INVENTION

The main objective of the present invention is to inhibit the activity of interleukins (IL 17 and IL 12/23), by using alstonine based novel composition.

Another objective of the present invention is to prepare alstonine topical formulations for treatment of skin related diseases.

DETAILED DESCRIPTION OF THE INVENTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with techniques of chemistry described herein are those well-known and commonly used in the art. In case of conflict, the present specification, including definitions, will control. The materials, methods, and examples are illustrative only and not intended to be limiting.

It must be noted that, as used in the specification and the appended claims, the singular forms "a," "an" and "the" include plural referents unless the context clearly dictates otherwise.

The term "comprising" as used herein is synonymous with "including" or "containing," and is inclusive or open-ended and does not exclude additional, unrecited members, elements or process steps.

The present invention relates to the interleukins (IL 17 and IL12/23) activity inhibiting composition. Further the present invention relates to the pharmaceutical composition for mitigating or minimizing the skin related disorders and or diseases.

Interleukin

Interleukins (ILs) are a group of cytokines (secreted proteins and signal molecules). The human genome encodes more than 50 interleukins and related proteins. The function of the immune system depends in a large part on interleukins, and rare deficiencies of a number of them have been described, all featuring autoimmune diseases or immune deficiency. The majority of interleukins are synthesized by helper CD4 T lymphocytes, as well as through monocytes, macrophages, and endothelial cells. They promote the development and differentiation of T and B lymphocytes, and hematopoietic cells.

Interleukin Inhibitors/Anti Interleukin

The 'interleukins' are 'cytokines', i.e. hormone-like molecules which can affect various cell functions thereby enabling communication between different cell types. Like other cytokines, interleukins are not stored within cells but are instead secreted rapidly, and briefly, in response to a stimulus, such as an infectious agent. Once an interleukin has been produced, it travels to its target cell and binds to it via a receptor molecule on the cell's surface. This interaction triggers a cascade of signals within the target cell that ultimately alter the cell's behavior. In the recent studies it has been shown that the sometimes without any present of any stimulus the interleukin get released and travel to cell which results in the various forms of diseases. In autoimmune and inflammation diseases interleukins are present in high elevated amount e.g. IL 6 in inflammation and diabetes, IL 1 in rheumatic disease and IL 17 and IL 12/23 in psoriasis and inflammatory skin disorders.

In order to treat the disease cause by the interleukins plenty of research ahs been going on the interleukin inhibitors. Interleukin inhibitors are immunosuppressive agents which inhibit the action of interleukins. Interleukins are a group of cytokines which are synthesized by lymphocytes, monocytes, macrophages, and certain other cells. Anti-interleukin (IL) therapies have emerged as a major treatment for patients suffering from the interleukin elevation. E.g. the interleukin IL-17 and IL-12/23 pathways are identified as playing the key roles in the immunopathogenesis of psoriasis. drugs like secukinumab are present in the market of the inhibition of the interleukin related diseases e.g. which is used for treating psoriasis, ankylosing spondylitis, and psoriatic arthritis. Also, lot of effort has been made on the development of monoclonal antibody of the ILs which can inhibits the IL activity and there has been some success in this regard. The Anti-human interleukin-6 (human IL-6) and anti-human IL-6 receptor (IL-6R)-neutralising monoclonal antibodies (mAbs) are among the most promising human IL-6-specific inhibitors and have been shown to exert short-term beneficial effects in clinical trials Alstonine Alstonine is an indole alkaloid and putative antipsychotic constituent of various plant species including *Alstonia boonei, Catharanthus roseus, Picralima nitida, Rauwolfia caffra* and *Rauwolfia vomitoria*. In preclinical studies alstonine attenuates MK-801-induced hyperlocomotion, working memory deficit and social withdrawal. It also possesses anxiolytic-like effects in preclinical studies, attenuates amphetamine-induced lethality and stereotypy as well as apomorphine-induced stereotypy, and attenuates haloperidol-induced catalepsy;

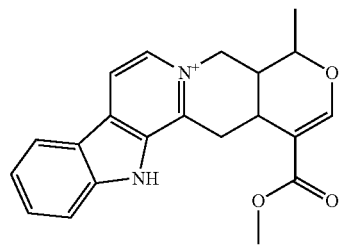 [SMILES: COC(=O)C1=COC(C)C2C[n+]3ccc4c([nH]c5ccccc54)c3CC12]

| Identifiers | |
|---|---|
| CAS Number | 642-18-2 |
| 3D model (JSmol) | Interactive image |
| ChemSpider | 149308 |
| PubChem CID | 441979 |
| Properties | |
| Chemical formula | $C_{21}H_{21}N_2O_3$ |

The present invention provides for the use of Alstonine in combination with other ingredients for effective treatment of number of skin related diseases such as psoriasis, eczema, acne, lichen planus, atopic dermatitis, seborrhic dermatitis, contact dermatitis, papules, pustules, ichthyosis, phemphigus etc.

One of the main natural sources of the Alstonine is the plant Alstonia boonei, Catharanthus *roseus, Picralima nitida, Rauwolfia caffra* and *Rauwolfia vomitoria'*. In the present invention the extracted Alstonine is used for the preparation of the compositions of the present invention. During the studies it was discovered that Alstonine is effective in inhibiting activity of interleukins (IL 17 and IL12/23). In the skin, interleukins are prominent cytokine that seems to be important in allergic and irritant contact dermatitis and inflammatory skin conditions. Modulating Interleukins in the skin may provide therapeutic benefits for a variety of skin conditions and the same has been achieved by the Alstonine based composition proposed by the present invention.

Accordingly, the present invention relates to an Alstonine based topical composition. The said composition includes DM Water, Glycerine, Alstonine, Cetyl palmitate, Glyceryl monostearate, Shea butter, Cetyl alcohol, Polysorbate 80, Cetostearyl alcohol, Coconut oil, Dimethicone, BHA, BHT, Phenoxyethanol, Ethylhexylglycerin (Euxyl PE 9010). The present composition is useful for inhibiting the interleukins (IL 17 and IL12/23) and treating skin disorder.

Accordingly, the present invention relates to interleukins (IL 17 and IL12/23) inhibiting topical composition comprising Alstonine, an emulsifier, an opacifier, a lubricant, a non-ionic surfactant and other known excipients including demineralized water. An emulsifier may define more than one class of compounds. An opacifier may define more than one class of compounds. A lubricant may define more than one class of compounds. A non-ionic surfactant may define more than one class of compounds. In other words, the interleukins (IL 17 and IL12/23) inhibiting composition according to the present invention may comprise more than one compound performing the same function; such as emulsification, as a surfactant, as a lubricant etc.

Accordingly, the present invention relates to topical composition comprising Alstonine compound, ester compounds, alcohol compounds, organic polymer compound along with other known excipients and demineralized water as a major constituent. The present invention composition inhibits the interleukins (IL 17 and IL12/23) and treats skin disorder.

Accordingly, the present invention relates to a pharmaceutical composition for topical application comprising demineralized water [DM Water], Alstonine compound, a fatty acid ester comprising 30 to 40 carbon atoms, an emulsifier [a glyceride compound, preferably a monoglyceride compound], an opacifier[e.g., a fatty alcohol [e.g., cetyl alcohol]], a lubricant [Ceto stearyl Alcohol], a non-ionic surfactant [Polysorbate 80], an organic polymer, preferably a silicone, [e.g., Dimethicone] as a surfactant and antifoaming agent and other ingredients as described in the examples as shown hereunder.

Accordingly, present invention relates to a method of preparing interleukins (IL 17 and IL12/23) inhibiting topical composition. The present invention includes DM Water, Glycerine, Alstonine, Cetyl palmitate, Glyceryl monostearate, Shea butter, Cetyl alcohol, Polysorbate 80, Cetostearyl alcohol, coconut oil, Dimethicone, BHA, BHT, Phenoxyethanol, Ethylhexylglycerin (Euxyl PE 9010). The method includes adding each ingredient simultaneously or individually one after the other to the DM water under stirring.

A method of preparation of the interleukins (IL 17 and IL12/23) activity inhibiting topical composition as claimed in claim 1, wherein each ingredient is added simultaneously or individually one after the other to the DM water under stirring.

The present invention provides for two types of Alstonine based formulations, where one is suitable for direct application(topical) on skin and other for oral administration.

Accordingly, the present invention relates to oral formulation comprising Alstonine, as the only major ingredient; and PVP 30 and Acrycoat s 100 in small quantities.

According to one embodiment of the present invention, table for topical composition.

TABLE 1

| S. No | INGREDIENT | WEIGHT PERCENTAGE |
|---|---|---|
| 1 | DM Water | 61.6% |
| 2 | Glycerine | 10.0% |
| 3 | Alstonine | 03.5% |
| 4 | Cetyl palmitate | 05.0% |
| 5 | Glyceryl monostearate | 03.7% |
| 6 | Shea butter | 03.0% |
| 7 | Cetyl alcohol | 04.0% |
| 8 | Polysorbate 80 | 01.5% |
| 9 | Ceto stearyl alcohol | 03.0% |
| 10 | Coconut oil | 03.0% |
| 11 | Dimethicone | 00.5% |
| 12 | BHA | 00.2% |
| 13 | BHT | 00.1% |
| 14 | Phenoxyethanol & Ethylhexylglycerin (Euxyl PE 9010) | 00.9% |

According to another embodiment of the present invention, table for topical composition.

TABLE 2

| S. No | INGREDIENT | WEIGHT PERCENTAGE |
|---|---|---|
| 1 | DM Water | 60.6% |
| 2 | Glycerine | 09.0% |
| 3 | Alstonine | 05.5% |
| 4 | Cetyl palmitate | 05.0% |
| 5 | Glyceryl monostearate | 03.0% |
| 6 | Shea butter | 03.7% |
| 7 | Cetyl alcohol | 04.0% |
| 8 | Polysorbate 80 | 01.5% |
| 9 | Ceto stearyl alcohol | 03.0% |
| 10 | Coconut oil | 03.0% |
| 11 | Dimethicone | 00.5% |
| 12 | BHA | 00.2% |
| 13 | BHT | 00.1% |
| 14 | Phenoxyethanol & Ethylhexylglycerin (Euxyl PE 9010) | 00.9% |

According to another embodiment of the present invention, table for oral composition.

TABLE 3

| S .No | INGREDIENTS | 5 mg Capsules |
|---|---|---|
| 1 | Alstonine | 4.0 mg |
| 2 | PVP 30 | 0.5 mg |
| 3 | Acrycoat s 100 | 0.5 mg |

In the present invention it is to be understood that the ingredients of topical composition have been described in weight by weight percentages. In case of oral formulation, the only main ingredient is Alstonine and the other two ingredients are known and added in a known weight as required by the person skilled in the art. The weight by weight percentages or the actual weights in oral formulation as shown in the examples are to be construed as illustrative purpose and the possible variations are understood to be included in the present invention as obvious modifications known to the skilled artisan.

The constituent compositions vary depending on the mode of application. For example, the present invention provides different compositions for topical and oral administrations for treating the skin related disorders or diseases. It may be construed that the present disclosure does not exclude the obvious additions and or modifications to the exclusive compositions as described and claimed through this invention.

The efficacy studies of the pharmaceutically active compound that is Alstonine was carried out by in-silico methods which had indicated a tremendous performance of the said active(s) in treating skin related disorders and or diseases.

Glyceryl Monostearate

GMS is a food additive used as a thickening, emulsifying, anticaking, and preservative agent; an emulsifying agent for oils, waxes, and solvents; a protective coating for hygroscopic powders; a solidifier and control release agent in pharmaceuticals; and a resin lubricant. It is also used in cosmetics and hair-care products.

GMS is largely used in baking preparations to add "body" to the food. It is somewhat responsible for giving ice cream and whipped cream their smooth texture. It is sometimes used as an antistaling agent in bread.

Cetyl Alcohol

Cetyl alcohol is used in the cosmetic industry as an opacifier in shampoos, or as an emollient, emulsifier or thickening agent in the manufacture of skin creams and lotions. It is also employed as a lubricant for nuts and bolts, and is the active ingredient in some "liquid pool covers" (forming a surface layer to reduce evaporation and retain heat).

Stearyl Alcohol

Stearyl alcohol (also known as octadecyl alcohol or 1-octadecanol) is an organic compound classified as a fatty alcohol with the formula CH3(CH2)16CH2OH. It takes the form of white granules or flakes, which are insoluble in water. It has a wide range of uses as an ingredient in lubricants, resins, perfumes, and cosmetics. It is used as an emollient, emulsifier, and thickener in ointments, and widely used as a hair coating in shampoos and hair conditioners. Stearyl heptanoate, the ester of stearyl alcohol and heptanoic acid (enanthic acid), is found in most cosmetic eyeliners. Stearyl alcohol has also found application as an evaporation suppressing monolayer when applied to the surface of water.

Stearyl alcohol is prepared from stearic acid or some fats by the process of catalytic hydrogenation. It has low toxicity.

Polysorbate 80

Food Use

Polysorbate 80 is used as an emulsifier in foods. For example, in ice cream, polysorbate is added up to 0.5% (v/v) concentration to make the ice cream smoother and easier to handle, as well as increasing its resistance to melting. Adding this substance prevents milk proteins from completely coating the fat droplets. This allows them to join together in chains and nets, which hold air in the mixture, and provide a firmer texture that holds its shape as the ice cream melts.

Health and Beauty Use

Polysorbate 80 is also used as a surfactant in soaps and cosmetics (including eyedrops), or a solubilizer such as in a mouthwash. The cosmetic grade of polysorbate 80 may have more impurities than the food grade.

Medical Use

Polysorbate 80 is an excipient that is used to stabilize aqueous formulations of medications for parenteral administration, and used as an emulsifier in the manufacture of the popular antiarrhythmic amiodarone. It is also used as an excipient in some European and Canadian influenza vaccines. Influenza vaccines contain 25 µg of polysorbate 80 per dose. It is also used in the culture of *Mycobacterium tuberculosis* in Middlebrook 7H9 broth. It is also used as an emulsifier in the estrogen-regulating drug Estrasorb.

Laboratory Use

Some mycobacteria contain a type of lipase (enzyme that breaks up lipid molecules); when these species are added to a mixture of polysorbate 80 and phenol red, they cause the solution to change color, so this is used as a test to identify the phenotype of a strain or isolate.

Dimethicone

Polydimethylsiloxane (PDMS) belongs to a group of polymeric organosilicon compounds that are commonly referred to as silicones. PDMS is the most widely used silicon-based organic polymer, and is particularly known for its unusual rheological (or flow) properties. PDMS is optically clear, and, in general, inert, non-toxic, and non-flammable. It is also called dimethylpolysiloxane or dimethicone and is one of several types of silicone oil (polymerized siloxane). Its applications range from contact lenses and medical devices to elastomers; it is also present in shampoos (as dimethicone makes hair shiny and slippery), food (antifoaming agent), caulking, lubricants and heat-resistant tiles.

Medicine and Cosmetics

Activated dimethicone, a mixture of polydimethylsiloxanes and silicon dioxide (sometimes called simethicone), is often used in over-the-counter drugs as an antifoaming agent and carminative. It has also been at least proposed for use in contact lenses.

Skin

PDMS is used variously in the cosmetic and consumer product industry as well. For example, PDMS can be used in the treatment of head lice on the scalp and dimethicone is used widely in skin-moisturizing lotions where it is listed as an active ingredient whose purpose is "skin protection." Some cosmetic formulations use dimethicone and related siloxane polymers in concentrations of use up to 15%. The Cosmetic Ingredient Review's (CIR) Expert Panel, has concluded that dimethicone and related polymers are "safe as used in cosmetic formulations."

Hair

PDMS compounds such as amodimethicone, are effective conditioners when formulated to consist of small particles and be soluble in water or alcohol/act as surfactants (especially for damaged hair, and are even more conditioning to the hair than common dimethicone and/or dimethicone copolyols.

Foods

PDMS is added to many cooking oils (as an antifoaming agent) to prevent oil splatter during the cooking process. As a result of this, PDMS can be found in trace quantities in many fast food items such as McDonald's Chicken McNuggets, french fries, hash browns, milkshakes and smoothies and Wendy's french fries.

Phenoxyethanol

Phenoxyethanol is a germicidal and germistatic glycol ether, phenol ether, and aromatic alcohol often used together with quaternary ammonium compounds.

Phenoxyethanol is used as a perfume fixative; an insect repellent; an antiseptic; a solvent for cellulose acetate, dyes, inks, and resins; a preservative for pharmaceuticals, cosmetics and lubricants; an anesthetic in fish aquaculture; and in organic synthesis.

Phenoxyethanol is an alternative to formaldehyde-releasing preservatives. In Japan and the EU, its concentration in cosmetics is restricted to 1%.

Phenoxyethanol is effective against gram-negative and gram-positive bacteria, and the yeast *Candida albicans*.

Ethylhexylglycerin

Ethylhexylglycerin, or octoxyglycerin, is a glyceryl ether that is commonly used as part of a preservative system in cosmetic preparations.

Glycerine

Glycerol is a colorless, odorless, viscous liquid that is sweet-tasting and non-toxic. The glycerol backbone is found in all lipids known as triglycerides. It is widely used in the food industry as a sweetener and humectant and in pharmaceutical formulations. Glycerol has three hydroxyl groups that are responsible for its solubility in water and its hygroscopic nature Glycerol is used in medical, pharmaceutical and personal care preparations, often as a means of improving smoothness, providing lubrication, and as a humectant. Ichthyosis and xerosis have been relieved by the topical use glycerin. It is found in allergen immunotherapies, cough syrups, elixirs and expectorants, toothpaste, mouthwashes, skin care products, shaving cream, hair care products, soaps, and water-based personal lubricants. In solid dosage forms like tablets, glycerol is used as a tablet holding agent. For human consumption, glycerol is classified by the U.S. FDA among the sugar alcohols as a caloric macronutrient.

Glycerol is a component of glycerin soap. Essential oils are added for fragrance. This kind of soap is used by people with sensitive, easily irritated skin because it prevents skin dryness with its moisturizing properties. It is believed to draw moisture up through skin layers and slows or prevents excessive drying and evaporation.

Glycerol can be used as a laxative when introduced into the rectum in suppository or small-volume (2-10 ml) enema form; it irritates the anal mucosa and induces a hyperosmotic effect.

Taken orally (often mixed with fruit juice to reduce its sweet taste), glycerol can cause a rapid, temporary decrease in the internal pressure of the eye. This can be useful for the initial emergency treatment of severely elevated eye pressure.

PVP

Povidone-iodine (PVP-I), also known as iodopovidone, is an antiseptic used for skin disinfection before and after surgery. It may be used both to disinfect the skin of the patient and the hands of the healthcare providers. It may also be used for minor wounds. It may be applied to the skin as a liquid or a powder.

Povidone-iodine is a broad-spectrum antiseptic for topical application in the treatment and prevention of wound infection. It may be used in first aid for minor cuts, grazes, burns, abrasions and blisters. Povidone-iodine exhibits longer lasting antiseptic effects than tincture of iodine, due to its slow absorption via soft tissue, making it the choice for longer surgeries. Chlorhexidine provides similar results, but with equal toxicity concerns.

Bacteria do not develop resistance to PVP-I.

Consequently, PVP-I has found broad application in medicine as a surgical scrub; for pre- and post-operative skin cleansing; for the treatment and prevention of infections in wounds, ulcers, cuts and burns; for the treatment of infections in decubitus ulcers and stasis ulcers; in gynecology for vaginitis associated with candidal, trichomonal or mixed infections. For these purposes PVP-I has been formulated at concentrations of 7.5-10.0% in solution, spray, surgical scrub, ointment, and swab dosage forms.

Because of these critical indications, only sterile povidone-iodine should be used in most cases. Non-sterile product can be appropriate in limited circumstances in which patients have intact, healthy skin that will not be compromised or cut. It should be noted that the non-sterile form of Povidone iodine has a long history of intrinsic contamination with *B. cepacia*, and other opportunistic pathogens. Its ability to harbor such microbes further underscores the importance of using sterile products in any clinical setting.

Cetyl Palmitate

Cetyl palmitate is the ester derived from palmitic acid and cetyl alcohol. Cetyl palmitate work as an emollient that lubricants and conditions the skin's surface, helping it to appear softer and smoother. It is also used as a surfactant in shampoos, and as an emulsifier and thickening agent in various lotions and creams.

Shea Butter

Shea Butter is a fat extracted from the nut of the African shea tree (*Vitellaria paradoxa*). It is usually yellow in color when raw, with more processed versions being ivory or white in color. Shea butter is a triglyceride (fat) derived mainly from stearic acid and oleic acid. It is widely used in cosmetics as a moisturizer, salve or lotion.

Cetostearyl Alcohol

Cetostearyl alcohol is a mixture of fatty alcohols, consisting predominantly of cetyl and stearyl alcohols and is classified as a fatty alcohol. It is used as an emulsion stabilizer, opacifying agent, and foam boosting surfactant, as well as an aqueous and nonaqueous viscosity-increasing agent. It imparts an emollient feel to the skin and can be used in water-in-oil emulsions, oil-in-water emulsions, and anhydrous formulations. It is commonly used in hair conditioners and other hair products.

BHA

A beta hydroxy acid or β-hydroxy acid (BHA) is an organic compound that contains a carboxylic acid functional group and hydroxy functional group separated by two carbon atoms. In cosmetics, the term beta hydroxy acid refers specifically to salicylic acid, which is used in some "anti-aging" creams and acne treatments. It is used to combat inflammation.

BHT

Butylated hydroxytoluene (BHT), also known as dibutylhydroxytoluene, is a lipophilic organic compound, chemically a derivative of phenol, that is useful for its antioxidant properties. BHT is listed under several categories in catalogues and databases, such as food additive, household product ingredient, industrial additive, personal care product/cosmetic ingredient, pesticide ingredient, plastic/rubber ingredient and medical/veterinary/research.

I claim:

1. A topical composition, the composition comprising of:
   61.6% of Demineralized (DM) Water;
   10.0% of Glycerine;
   03.5% of Alstonine;
   05.0% of Cetyl palmitate;
   03.7% of Glyceryl monostearate;
   03.0% of Shea butter;
   04.0% of Cetyl alcohol;
   01.5% of Polysorbate 80;
   03.0% of Ceto stearyl alcohol;
   03.0% of Coconut oil;
   00.5% of Dimethicone;

00.2% of Beta Hydroxy Acid (BHA);
00.1% of Butylated Hydroxytoluene (BHT);
00.9% of Phenoxyethanol; and
00.9% of Ethylhexylglycerin (Euxyl PE 9010),
wherein said composition inhibits the interleukins (IL 17 and IL12/23) activity and treats skin disorder.

2. A topical composition, the composition comprising of:
60.6% of DM Water;
09.0% of Glycerine;
05.5% of Alstonine;
05.0% of Cetyl palmitate;
03.0% of Glyceryl monostearate;
03.7% of Shea butter;
0.40% of Cetyl alcohol;
01.5% of Polysorbate 80;
03.0% of Ceto stearyl alcohol;
03.0% of Coconut oil;
00.5% of Dimethicone;
00.2% of Beta Hydroxy Acid (BHA);
00.1% of Butylated Hydroxytoluene (BHT);
00.9% of Phenoxyethanol; and
00.9% of Ethylhexylglycerin (Euxyl PE 9010),
wherein said composition inhibits the interleukins (IL 17 and IL12/23) activity and treats skin disorder.

3. An oral formulation for 5 mg capsule, the formulation comprises of:
4.0 mg of Alstonine;
0.5 mg of PVP 30; and
0.5 mg of Acrycoat s 100.

4. A method of preparation of the interleukins (IL 17 and IL12/23) activity inhibiting topical composition as claimed in claim 1, wherein each ingredient of the composition is added simultaneously or individually one after the other to the DM water under stirring.

* * * * *